United States Patent
Elyasaf et al.

(10) Patent No.: US 7,326,901 B2
(45) Date of Patent: Feb. 5, 2008

(54) HIGH THROUGHPUT MULTI BEAM SYSTEM AND METHOD

(75) Inventors: Emanuel Elyasaf, Rehovot (IL); Steven R. Rogers, Emek Sorek (IL)

(73) Assignee: Applied Materials, Israel, Ltd., Rehovot (IL)

( * ) Notice: Subject to any disclaimer, the term of this patent is extended or adjusted under 35 U.S.C. 154(b) by 345 days.

(21) Appl. No.: 10/910,117

(22) Filed: Aug. 2, 2004

(65) Prior Publication Data
US 2006/0023205 A1    Feb. 2, 2006

Related U.S. Application Data
(60) Provisional application No. 60/562,722, filed on Apr. 15, 2004.

(51) Int. Cl.
*H01L 27/00* (2006.01)
(52) U.S. Cl. ............................. 250/208.1; 250/559.08
(58) Field of Classification Search ............. 250/208.1, 250/216, 559.05–559.08, 559.46; 356/237.2, 356/237.4, 237.5
See application file for complete search history.

(56) References Cited

U.S. PATENT DOCUMENTS

| | | | |
|---|---|---|---|
| 4,731,855 A | 3/1988 | Suda et al. | |
| 5,241,369 A | 8/1993 | McNeil et al. | |
| 6,038,018 A | 3/2000 | Yamazaki et al. | |
| 6,122,046 A | 9/2000 | Almogy | |
| 2003/0085335 A1* | 5/2003 | Almogy et al. | 250/208.1 |
| 2004/0061042 A1 | 4/2004 | Almogy et al. | |

OTHER PUBLICATIONS

Search Report, "International Searching Authority", PCT/US2005/012917, (Jun. 12, 2005),13 pgs.

* cited by examiner

*Primary Examiner*—Kevin Pyo
(74) *Attorney, Agent, or Firm*—Tarek N. Fahmi (57) ABSTRACT

A system and method for inspecting an article, the system includes a spatial filter that is shaped such as to direct output beams towards predefined locations and an optical beam directing entity, for directing the multiple output beams toward multiple detector arrays. The method includes spatially filtering multiple input light beams to provide substantially aberration free output light beams; and directing the multiple output beams by an optical beam directing entity, toward multiple detector arrays.

2 Claims, 13 Drawing Sheets

HIGH THROUGHPUT MULTI BEAM SYSTEM AND METHOD

The present patent application is a non-provisional application claiming the priority of U.S. Provisional Patent Application No. 60/562,722, filed Apr. 15, 2004.

BACKGROUND OF THE INVENTION

1. Field of the Invention

The present invention relates to a system and a method for detecting an array of light spots and especially for allowing high throughput detection of multiple spots that involves spot spatial distortion correction. The array of spots is usually utilized for inspecting an article such as but not limited to a wafer, a reticle and the like.

2. Description of the Related Art

The inspection of semiconductor wafers is typically performed by scanning a laser beam across a wafer's surface and collecting light scattered therefrom. The scanning operation is conducted by scanning the laser beam across the wafer surface in a first direction using one of a variety of known deflectors, such as acousto-optic deflectors or electromechanical deflectors, while moving a stage that supports the wafer thereon in a second direction, which is typically orthogonal to the first direction. Another type of inspection includes illuminating an area and acquiring an image. U.S. Pat. No. 5,699,477 of Alumot et al, U.S patent as well of U.S. Pat. No. 6,693,664 of Neumann provide examples of such inspection systems.

There is a greater emphasis on the throughput of inspection devices and accordingly on the throughput of scanners, as the design rules for semiconductors rapidly shrink without a corresponding decrease of the inspection sequence time period or the overall size of semiconductor dies or wafers.

High throughput inspection systems utilizes optical beam arrays as well as electron beam arrays for increasing throughput. Hybrid systems that include electron beam illumination, electro-optical conversion and light beam detection are also known. Electron beams also provide higher resolution. U.S. Pat. No. 6,671,042 of Almogy, U.S. Pat. No. 6,639,201 of Almogy et al., U.S. Pat. Nos. 6,578, 961 and 6,208,411 of Vaez-Iravani, U.S. Pat. No. 6,248,988 of Krantz, which are incorporated herein by reference, describe state of the art inspection systems.

The beams that form a beam array may be spatially distorted during the illumination as well as during the collection/detection stages of the article inspection process. Different beams may be distorted in a different manner. Furthermore, the distortion can change over time.

Various image processing methods are known in the art. They include die-to-die comparison, cell-to-cell comparison and die to database comparison. These comparisons require knowledge of the location of obtained pixels. In other words, spatial distortions can result in a comparison between pixels from different locations of compared dies of cells.

There is a need for a system and method for compensating for spatial distortions.

SUMMARY OF THE INVENTION

A system and method for high throughput wafer inspection that compensates for various aberrations of an array of light beams.

A system that includes a spatial filter that is shaped such as to direct output beams towards predefined locations and an optical beam directing entity, for directing the multiple output beams toward multiple detector arrays.

A method for inspecting an article, the method includes spatially filtering multiple input light beams to provide substantially aberration free output light beams, and directing the multiple output beams by an optical beam directing entity, toward multiple detector arrays.

A system that includes multiple detector arrays and an optical beam directing entity that comprises multiple beam directing elements, whereas the multiple beam directing elements are shaped such as to direct multiple beam portions towards the multiple detector arrays at a predefined manner, substantially regardless of spatial distortions of the beams.

A system that includes multiple detector arrays, and an optical beam directing entity, for directing multiple beams towards multiple detector arrays in an interlaced manner.

A method for compensating for spatial aberrations of an array of light beams, the method includes: determining a spatial distortion pattern of the array of light beams; and configuring a optical component in response to the distorted aberrations such as to provide a substantially non-distorted array of light beams.

A method for inspecting an article, the method includes: receiving multiple light beams; and directing, by an optical beam directing entity, multiple beams towards multiple detector arrays in an interlaced manner.

Other features of the present invention will become apparent from the following detailed description considered in connection with the accompanying drawings that disclose embodiments of the present invention.

BRIEF DESCRIPTION OF THE DRAWINGS

The foregoing and other objects, features, and advantages of the present invention will become more apparent from the following detailed description when taken in conjunction with the accompanying drawings. In the drawings, similar reference characters denote similar elements throughout the different views, in which.

DETAILED DESCRIPTION OF THE PREFERRED EMBODIMENTS

Reference will now be made in greater detail to exemplary embodiments of the present invention. In the following description made in conjunction with the exemplary embodiments of the present invention, a variety of specific elements are described. The following detailed description is of exemplary embodiments of the invention but the invention is not limited thereto, as modifications and supplemental structures may be added, as would be apparent to those skilled in the art. Also, in the following description of the present invention, a detailed description of known functions and configurations incorporated herein is omitted.

In particular, but without limitation, while an exemplary embodiment may be disclosed with regard to the inspection of an article surface by detecting reflected light using a light source and detecting unit that are disposed on a common side of an article (a "reflective system"), it would be readily apparent to one skilled in the art that the teachings are readily adaptable to the inspection of an article by detecting transmitted light with a detecting unit that is on a side of an article opposite to that of the light source (a "transmissive system"). While the reflective system and the transmissive system differ, for one example by the absence of a beam splitter in the transmissive system, the principles of the present invention are applicable to both types of systems. As would be understood by one skilled in the art, both types of systems may be utilized separately or together in an inspection of an article. Furthermore, it is to be understood that all listed values are provided for sake of the explanation and are not binding.

Figure 1:
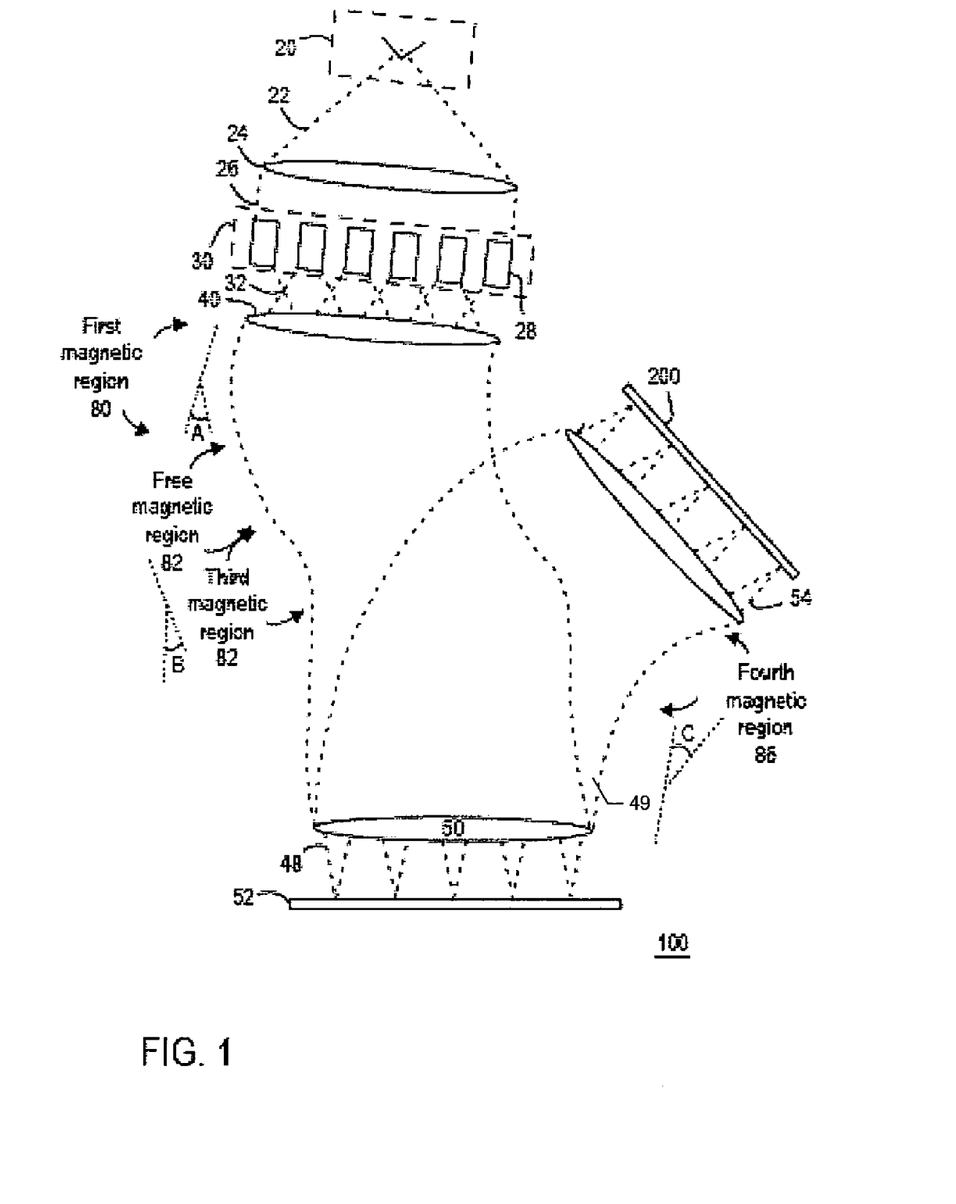
FIG. 1 illustrates an exemplary embodiment of an inspection system, according to an embodiment of the invention.

FIG. 1 illustrates an exemplary embodiment of an inspection system 100, according to an embodiment of the invention.

The inspection system 100 directs multiple electron beams, such as an array of 100×100 beams 48 onto an inspected object 52, receives secondary electrons 49 emitted from the object 52, and eventually converts the array of electron beams to light beams by scintillator 200. System 100 includes an electron source arrangement 20 that generates a diverging beam 22 which is collimated by collimating lens 24 to form a substantially collimated electron beam 26. This beam illuminates a multiple-aperture arrangement 30 that defined multiple apertures by a multiple aperture plate 28. For simplicity of explanation only five apertures were illustrated. The multiple aperture plate 28 can have various alternative configurations. It is assumed that it forms a staggered array that includes 10000 apertures. The collimated electron beam 26 passes through the multiple aperture plate 28 to provide 10000 electron beams. The multiple aperture plate further focuses each of these electron beams at a first plane, to provide an intermediate image denoted by focal points 32. An imaging lens 40 and objective lens 50 image the intermediate image onto an article. The imaging lens 40 and objective lens 50 are oriented in respect to each other, for example by ninety degrees, in order to separate the primary beam path from the secondary beam path. In other words, the beams that pass through imaging lens 40 propagate at a complex path till they pass through objective lens 50 that in turn focuses them onto the inspected object 52. The path is "bent" using electromagnetic components, in a manner known in the art. For example, the beams can first pass through an homogenous magnetic field (represented by first magnetic region 80) deflecting the beams by a certain angle A to the left. They can than pass a drift region that is free of magnetic fields (represented by second magnetic region 82). They then can pass through another homogenous magnetic field (represented by third magnetic region 84) that deflects the beams by another angle B such as to enter the objective lens 50 in about ninety degrees to the objective lens 50. The secondary beams form a secondary image on the surface of the inspected object 52 that is then imaged onto the scintillator 200. The secondary primary beams propagate across a complex path, which is "bent" to the right by a third angle C (represented by fourth magnetic region 86).

According to an embodiment of the invention the light beams are arranged such as to form a rectangular array. According to another embodiment the light beams are arranged such as to form a staggered (or graded) array in which even rows and odd rows are misaligned by a predefined distance. For convenience of explanation only the latter formation is illustrated.

Figure 2:
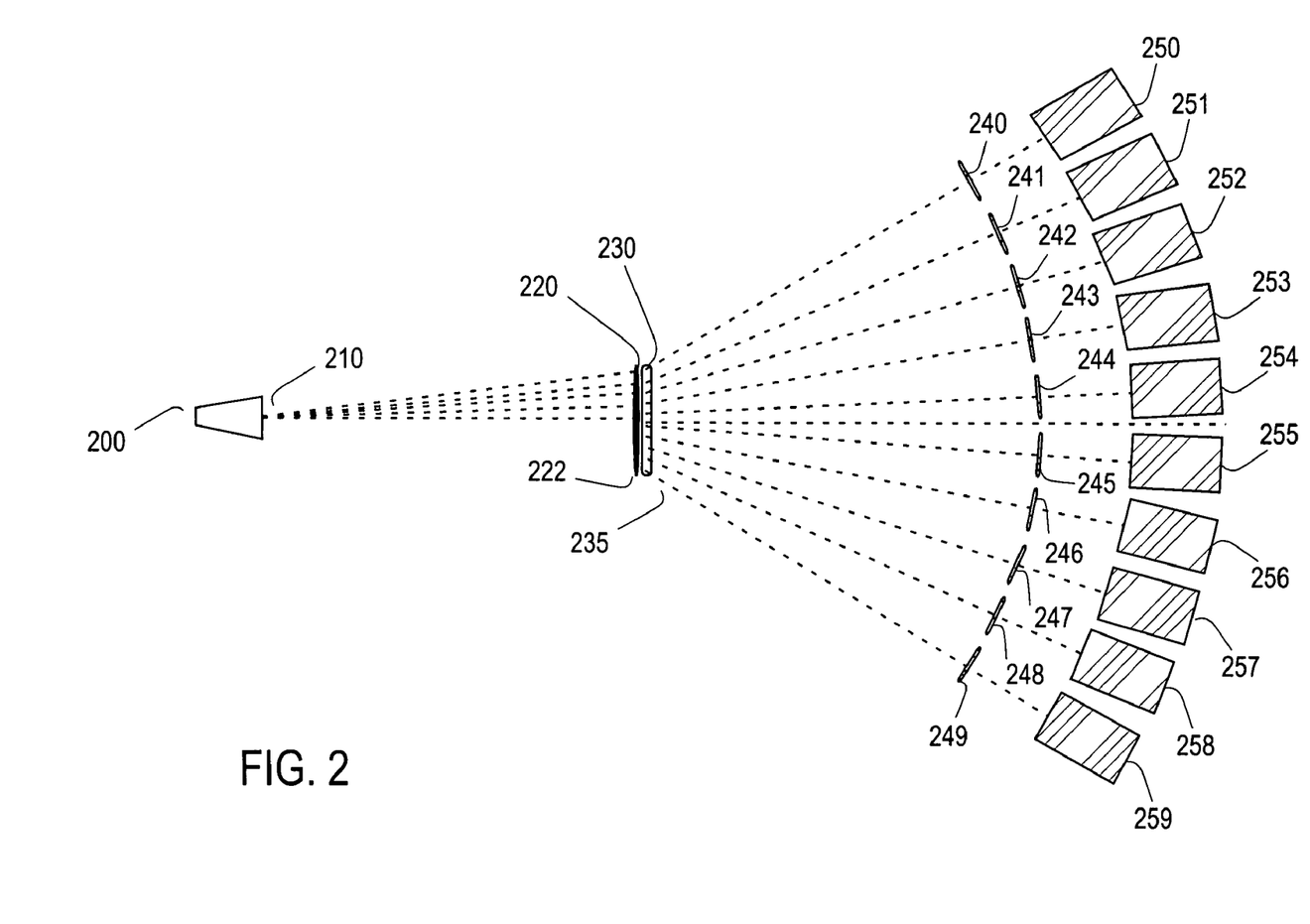
FIG. 2 illustrates various optical components, according to an embodiment of the invention.

FIG. 2 illustrates various optical components, according to an embodiment of the invention. An array of electron beams is directed towards an electron to light converter, such as scintillator 200. Scintillator 200 provides a distorted array of 100×100 light beams that are spaced apart from each other by a distance of substantially (due to distortions) of 0.1 mm to form an array of about 10×10 mm. This array is magnified by an optical arrangement that includes a magnifying lens 210 that is followed by an optional field lens 220, a spatial filter 230 and a Fresnel array 235. The optional field lens 220 enables to utilize relatively concise optical components that are capable of managing beam rows that include many beams.

The 10×10 mm array is magnifies by the magnification lens 210 by a factor of ten to form an intermediate image 222 of 100×100 mm at field lens 220. The magnifying lens 210 has a Numerical Aperture (NA) of 0.5. The space between the magnifying lens 210 and the scintillator 200 is filled with a fluid that is characterized by an immersion index of n=1.83.

According to an embodiment of the invention the spatial filter 230 and a Fresnel array 235 are positioned in proximity to each other, and they may also be integrally formed. The spatial filter 230 may be printed on one of the facets of the Fresnel array 235.

The Fresnel array 235 directs various portions of the intermediate image, via multiple imaging lenses 240-249 towards multiple detector arrays (also referred to as sensor arrays) 250-259. Each imaging lens 240-249 is characterized by a de-magnification factor of 4.

Figure 3:
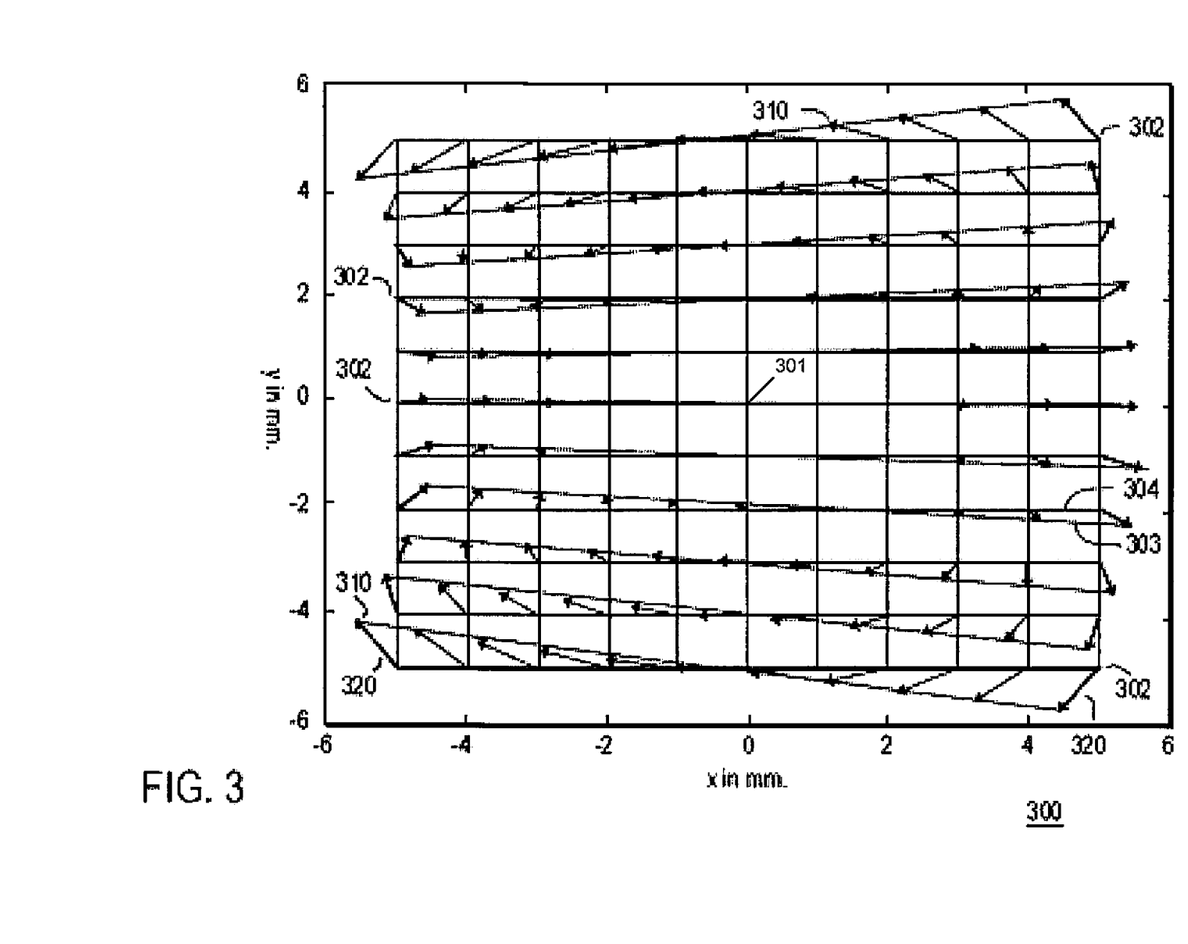
FIG. 3 illustrates a simulated distortion map, according to an embodiment of the invention.

FIG. 3 illustrates a simulated distortion map 300, according to an embodiment of the invention. This map is out of scale. For example, the spacing between undistorted points is about several millimeters while the distortion is in the range of microns.

As can be seen by the simulated distortion map 300 instead of a regular array (illustrated by points 302) a distorted array (illustrated by points 310) is formed at the plane of the spatial filter 230. Arrows 320 illustrates the distortion. The maximal distortion is denoted MaxD. Lines 304 plots the undistorted grid while lines 303 plots the distorted grid.

The inventors found that by blocking the perimeter of each input beam, and especially a ring-shaped perimeter that is responsive to MaxD, an output beam that passes said blocking will be free of distortions, in the sense that it will be directed to a predefined location, substantially regardless of the distortion.

Thus, by placing spatial filter 230 at the path of light beams the system converts spatial distortions to amplitude variations. In cases where the distortions are invariant (time independent) this conversion does not introduce an error to die-to-die comparison method and even to other comparison methods.

Figure 4:
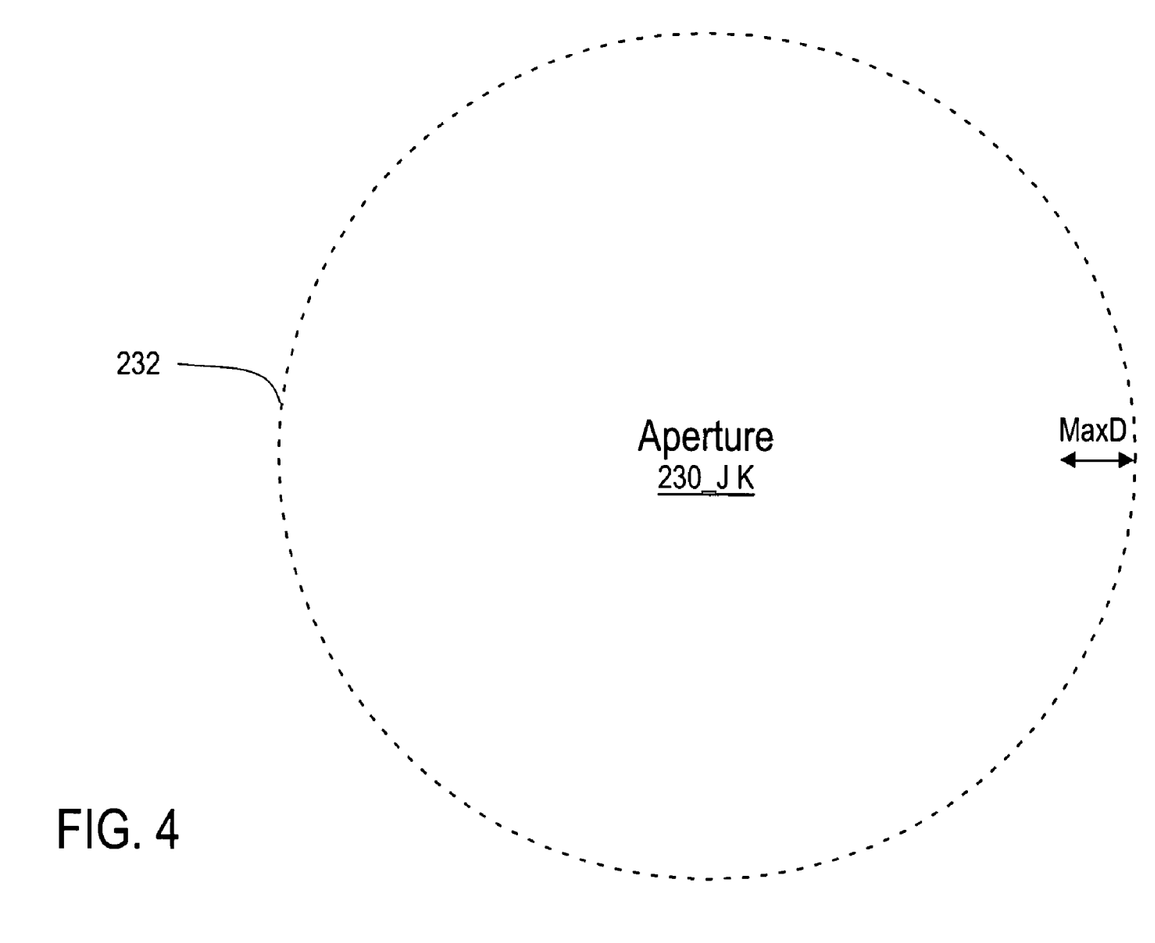
FIG. 4 illustrates a single aperture of the spatial filter and the relationship between the expected beam distortion and the shape and size of the aperture; according to an embodiment of the invention.

FIG. 4 illustrates a single aperture 230_j,k of spatial filter 230. The dashed line 232 represents a cross section of an output beam. The aperture diameter is smaller than the diameter of the input beam by MaxD. Thus, even if the input beam is distorted by the maximal expected distortion, the aperture 230_j,k passes only a non-distorted output beam.

Figure 5A:
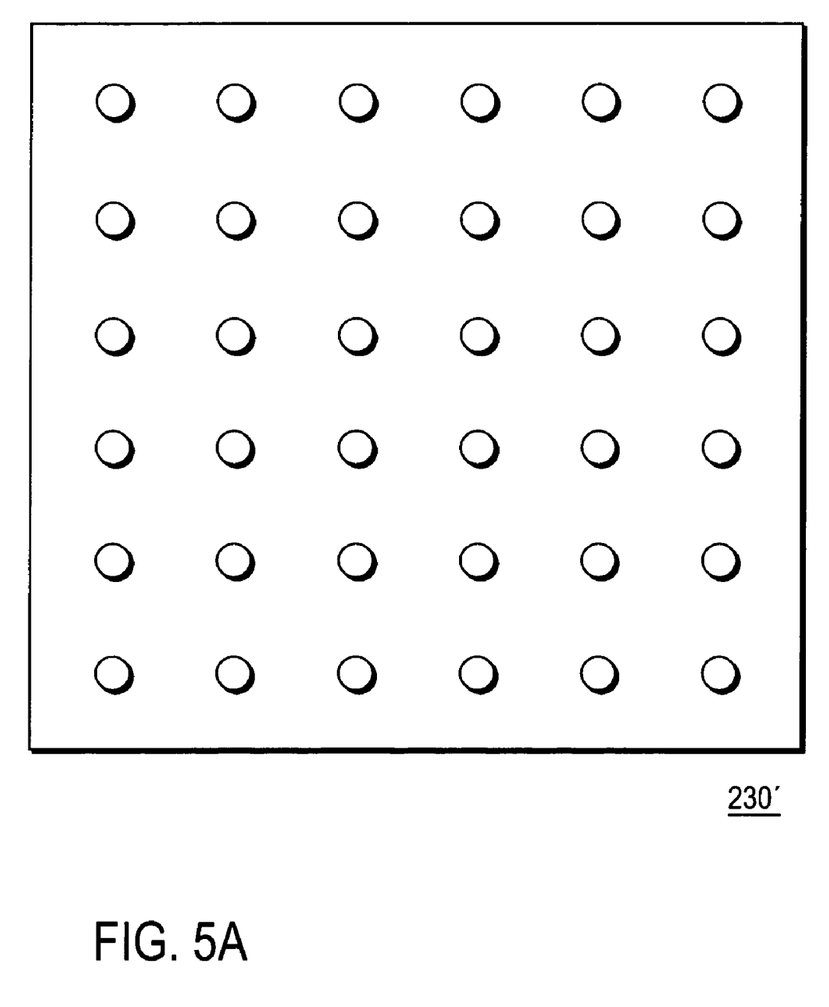
FIGS. 5a-5b illustrates various portions of spatial filters, according to various embodiments of the invention.
Figure 5B:
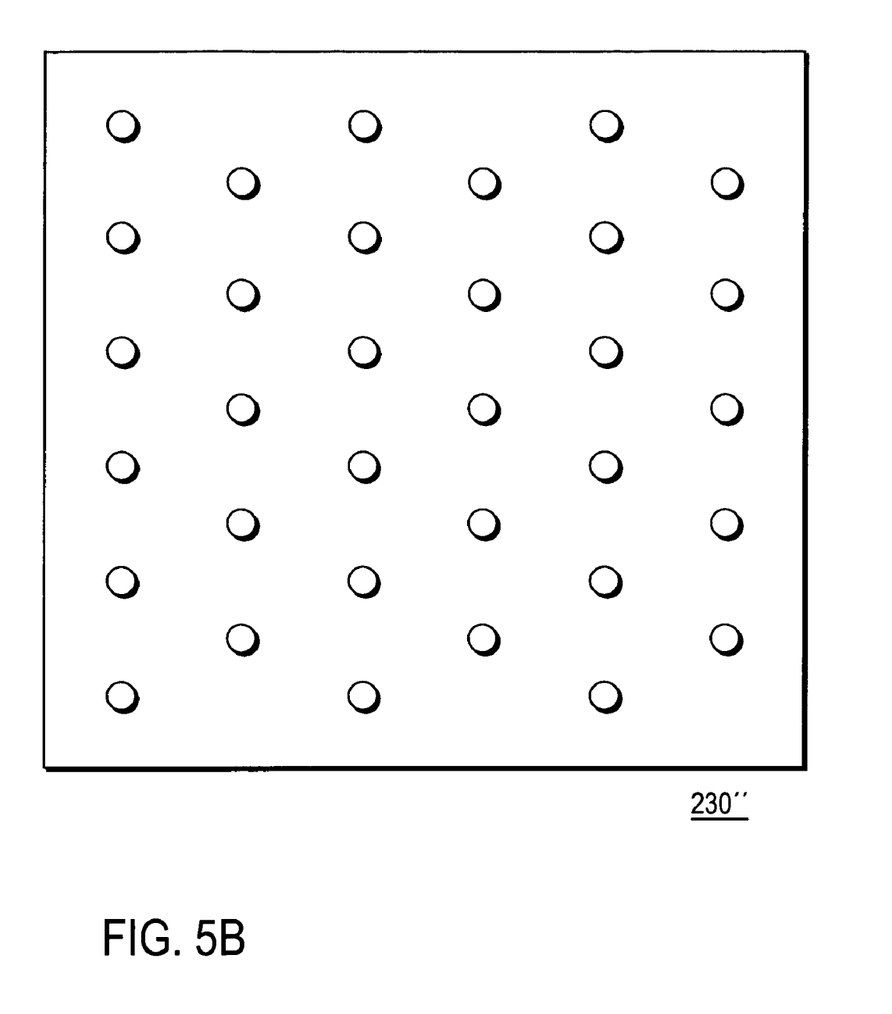

FIGS. 5a-5b illustrate various portions of spatial filters 230' and 230", according to various embodiments of the invention. Spatial filter 230' defines multiple apertures that are arranged in an ordered manner. Spatial filter 230" includes multiple apertures that are re-arranged in response to the shape of the distorted beam array. For example, map 300 illustrates that rows that are more distant than an imaginary array center 301 are more oriented in respect to an imaginary horizon than rows that are more close to the center 301. Rows that belong to the upper half of the array are oriented in a positive angle in relation to an imaginary horizon while rows that belong to the lower half of the array are oriented in a negative angle in relation to such an imaginary horizon.

The inventors found that by positioning the apertures of the spatial array in oriented rows, responsive to the expected distortions, a larger amount of light can pass through each aperture.

As illustrated by the dashed lines (illustrative of light paths) of FIG. 2, each pair of adjacent sensor arrays {(250, 251), (252, 253), (254, 255), (256, 257) and (258, 259)} receives beams that are positioned within a single portion of the intermediate image 222. As better illustrated in FIGS. 6-8, this arrangement (also referred to as an interlaced arrangement) allows utilizing multiple high-speed line sensors. Conveniently, each line of light sensitive elements is connected to a high-speed shift register.

Figure 6:
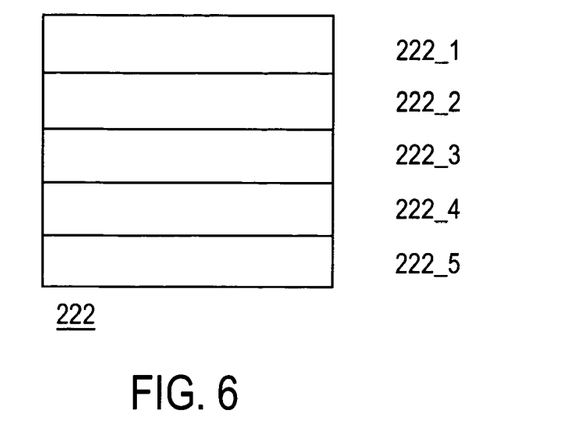
FIG. 6 illustrates five portions of an intermediate image according to an embodiment of the invention.

FIG. 6 illustrates five portions 222_1-222_5 of intermediate image 222. Each pair of sensor arrays receives a corresponding image portion. A first portion 222_1 is imaged onto sensor arrays 250 and 251. A second portion 222_2 is imaged onto sensor arrays 252 and 253. A third portion 222_3 is imaged onto sensor arrays 254 and 255. A fourth portion 222_4 is imaged onto sensor arrays 256 and 257. A fifth portion 222_4 is imaged onto sensor arrays 258 and 259.

Figure 7A:
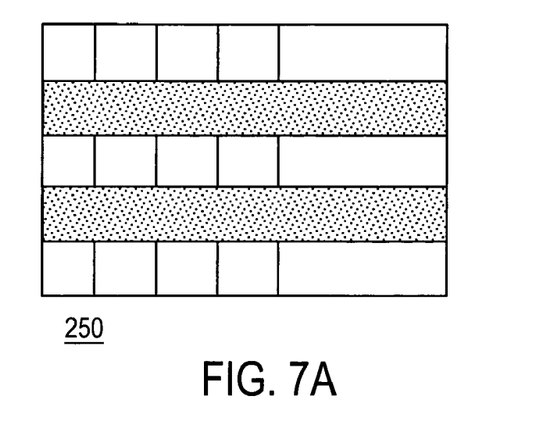
FIG. 7 illustrates a portion of a sensor array, according to an embodiment of the invention.
Figure 7B:
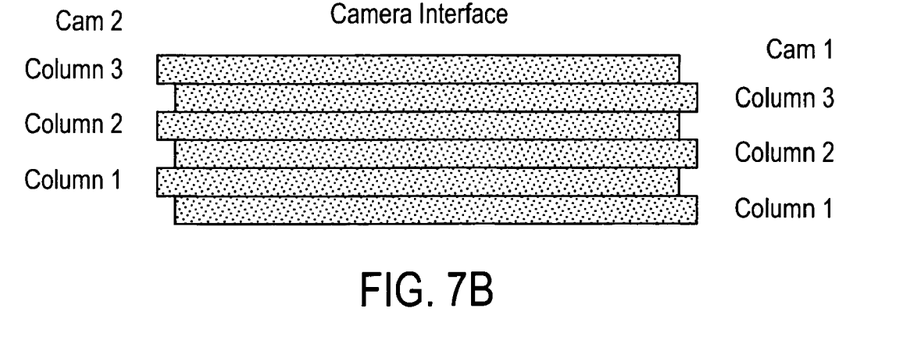

FIG. 7 illustrates a portion 250' of sensor array 250. Sensor array 250 includes one hundred line CCDs. Each line CCD is a one dimensional sensor array. Each line CCD includes a row of CCD light sensitive cells, such as cells 250_1_1-250_1j. These cells are connected in parallel to a high-speed parallel to serial shift register 250'_1 that includes one hundred shift register cells, such as shift register cells 250'_1_1-250'_1_j. The shift register cells as well as the light sensitive cells are positioned on a frontal facet of each sensor array. The shift register cells form gaps in the light sensitive areas of each sensor array facet. As illustrated in more details in further figures, light is directed towards pairs of sensor arrays such that a line CCDs of a first sensor array 251 is positioned such as to receive light that propagates towards shift register cells of another sensor array. This configuration is referred as an interlaced configuration.

Figure 8:
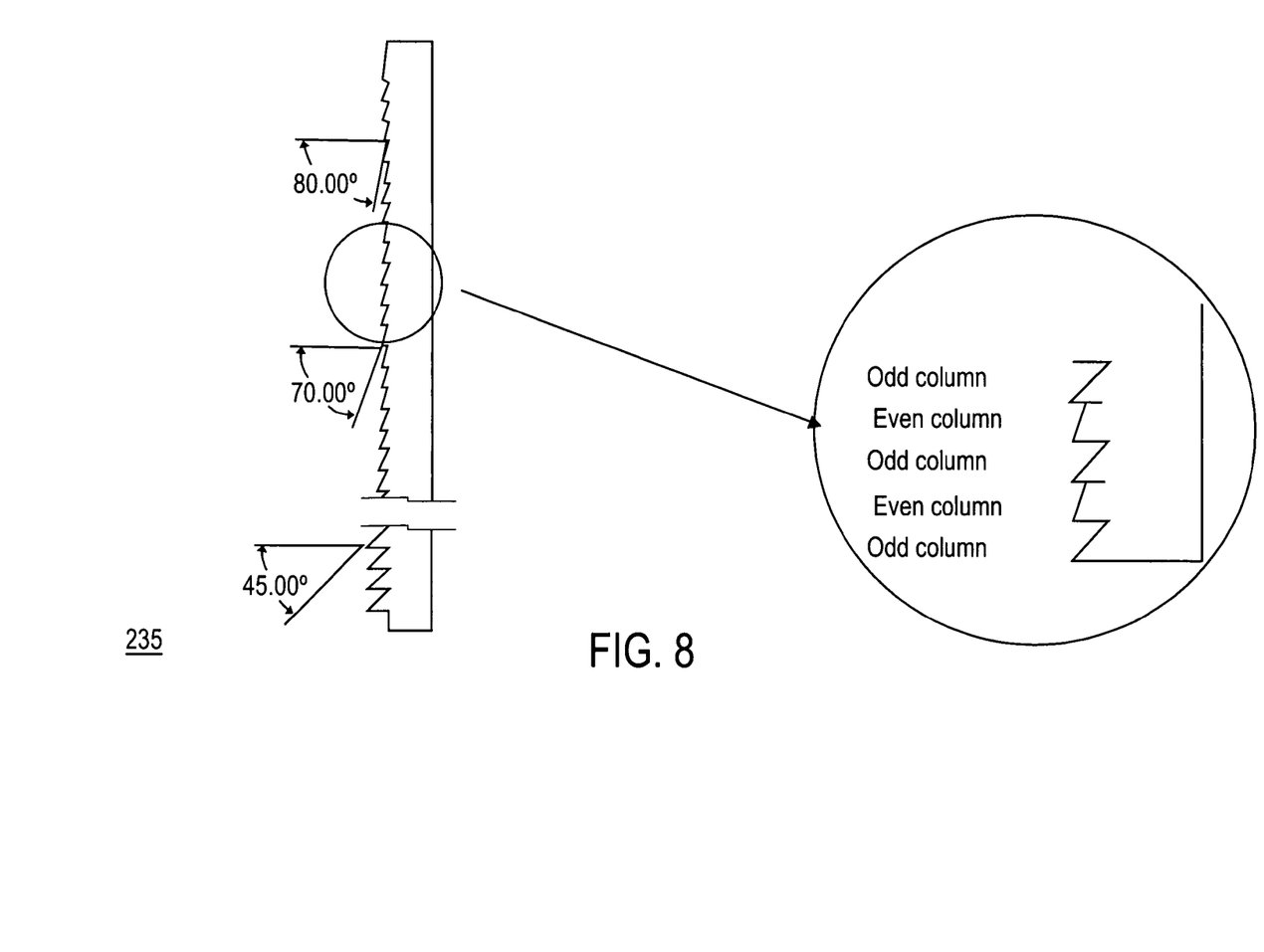
FIG. 8 is a cross sectional view of a Fresnel lens array, according to an embodiment of the invention.
Figure 9:
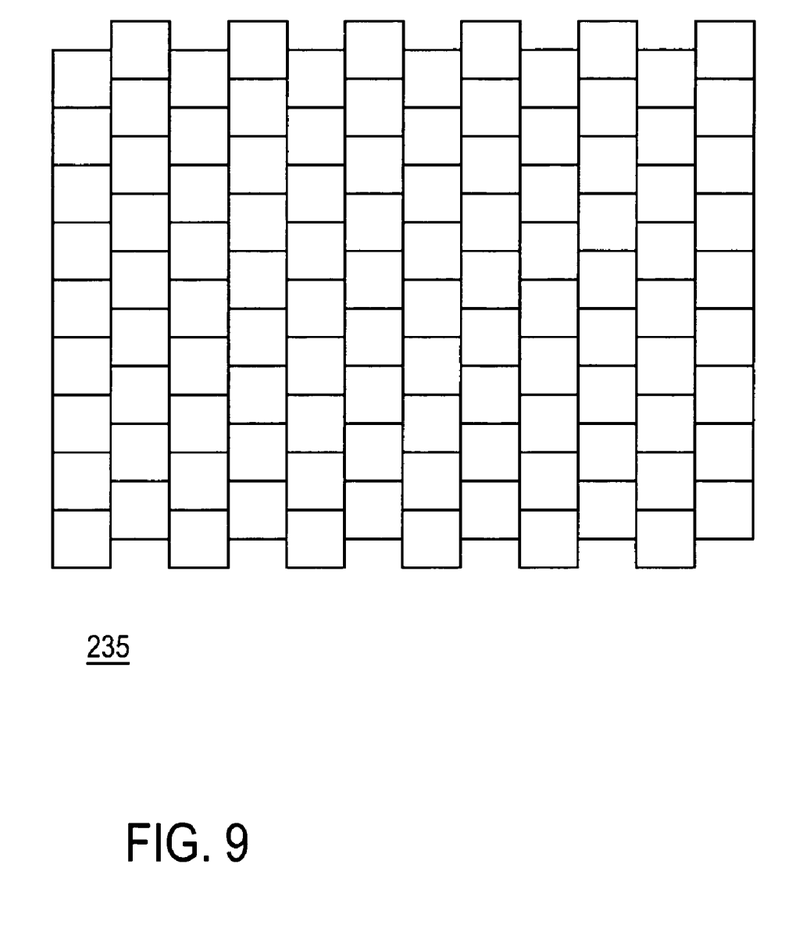
FIG. 9 is a front view of a Fresnel lens array, according to an embodiment of the invention.

FIG. 8 is a cross sectional view of a Fresnel lens array 235, and FIG. 9 is a front view of that Fresnel lens array 235, according to an embodiment of the invention. Fresnel lens array 235 includes multiple (such as 100×100) lenses, that form a two dimensional array of lenses. Each lens directs a single beam that passed through an aperture of spatial filter 230, via an imaging lens, towards a single CCD cell.

According to an embodiment of the invention the spatial filter is positioned after the Fresnel lens array. For example, a shaped aperture can be printed to each Fresnel lens.

The lenses of the Fresnel lens array 235 are positioned in accordance with the paths of substantially non-distorted light beams.

The first twenty rows of Fresnel lenses direct light beams from portion 222_1 towards sensor arrays 250 and 251. More specifically, lenses that belong to odd rows of the Fresnel lens array 235 direct light beams towards corresponding line CCDs of sensor array 250 while Fresnel lenses that belong to even rows of the Fresnel lens array 235 direct light beams towards corresponding line CCDs of sensor array 251. It is further noted that each row of Fresnel lenses can be translated by a predefined distance (such as half of a lens length) from an adjacent row of lenses.

The inventors found that by adapting this interlaced arrangement, rectangular CCD arrays can be used.

Figure 10:
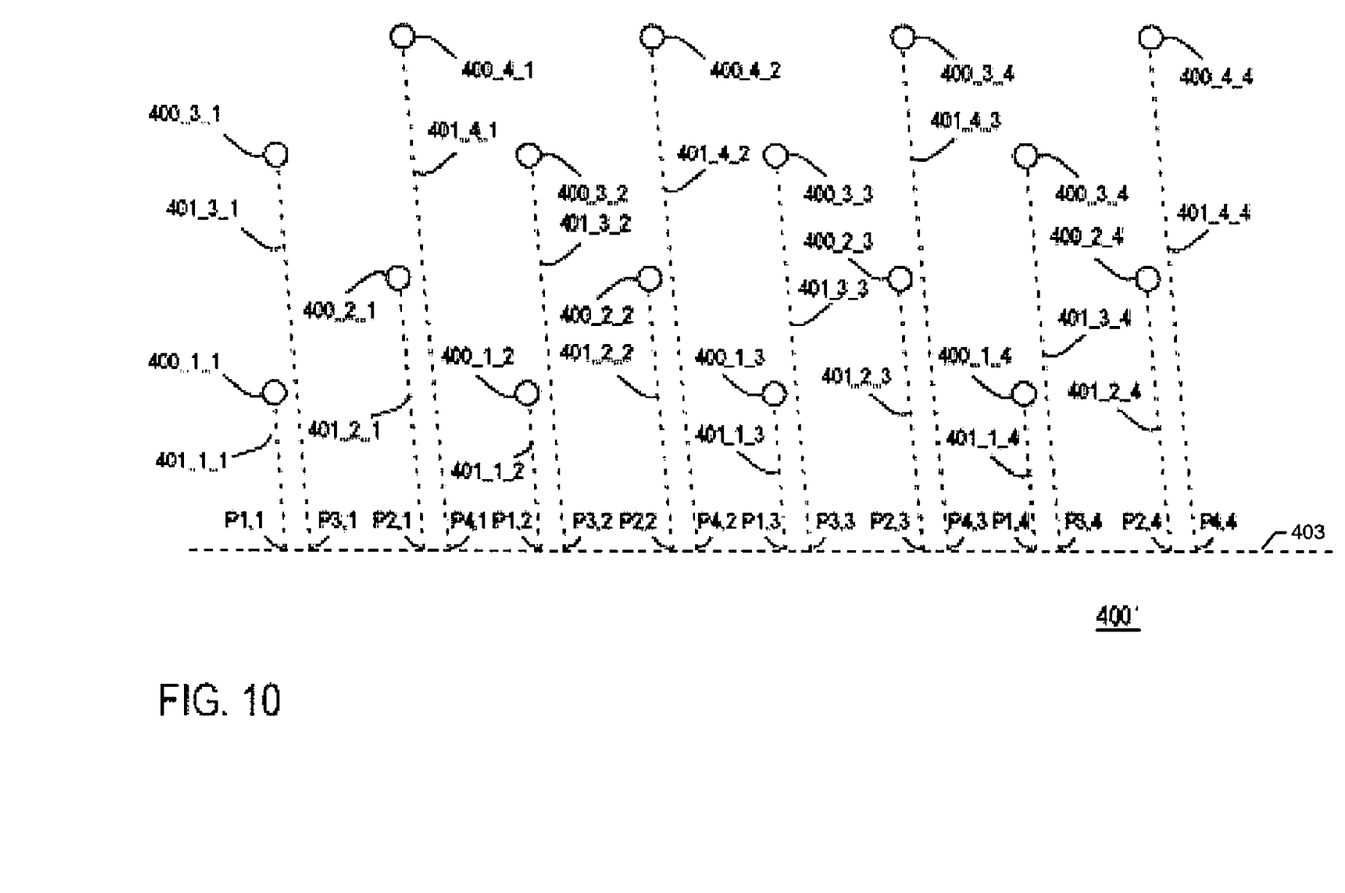
FIG. 10 illustrates sixteen spots that are arranged in four rows, as well as their scan paths, according to an embodiment of the invention.

FIG. 10 illustrates sixteen spots that are arranged in four rows, as well as their scan paths. A mechanical system moves the imaged article in a direction which is nearly parallel to an axis (such as an imaginary y-direction) of the spots such that as the article is moved across the spot array in the scan direction (the y-direction) the spots traces a path which leaves no gaps in the mechanical cross-scan direction (the x-direction). The scan paths are illustrated by dashed lines. The first row includes spots 400_1_1-400_1_4. These spots scan an article along scan paths 401_1_1-401_1_4. The second row includes spots 400_2_1-400_2_4. These spots scan an article along scan paths 401_2_1-401_2_4. The third row includes spots 400_3_1-400_3_4. These spots scan an article along scan paths 401_3_1-401_3_4. The fourth row includes spots 400_4_1-400_4_4. These spots scan an article along scan paths 401_4_1-401_4_4.

The most upper row is the fourth row, and it is followed by ninety-six rows to provide an array that includes one hundred rows. Each row further includes ninety-six spots to provide a row of one hundred spots.

Within the system various images of these spots are provided. A first image is formed on the inspected article. Another image is formed at the scintillator plane. Yet another image (previously referred to as an intermediate image) is formed at the spatial filter. This intermediate image 222 is split and de-magnified to provide multiple image portions on the sensor arrays. For simplicity of explanation the following description will refer to the intermediate image.

The intermediate image is about 100×100 mm. The distance between adjacent spots that belong to the same row is 1 mm. The vertical displacement between adjacent rows is 1 mm. The spots of the odd rows are horizontally displaced in relation to corresponding spots of the even rows by 0.5 mm.

An imaginary horizontal line 403 is crossed by the scan lines 401_1_1-401_4_4 at multiple imaginary points denoted P1,1-P4,4. The imaginary horizontal line 403 is first crossed by spots 400_1_1-400_1_4, than by spots 400_2_1-

400_2_4, followed by spots 400_3_1-400_3_4 and finally is crossed by spots 400_4_1-400_4_4.

Due to the horizontal displacement between rows the spot array includes two hundred columns, each column includes fifty spots. The odd columns include spots that define the odd rows and the even columns include spots that define the even columns. For example, spots 400_1_1 and 400_3_1 define a first column and belong to odd rows. Each column crosses the imaginary horizontal line 403 to form a continuous line portion.

Due to the vertical displacement between rows, the even and odd rows cross the imaginary horizontal line 403 in an interlaced manner. By using interlaced sensor arrays, each sensor array receives a stream of spots that form a continuous line portion.

Figure 11:
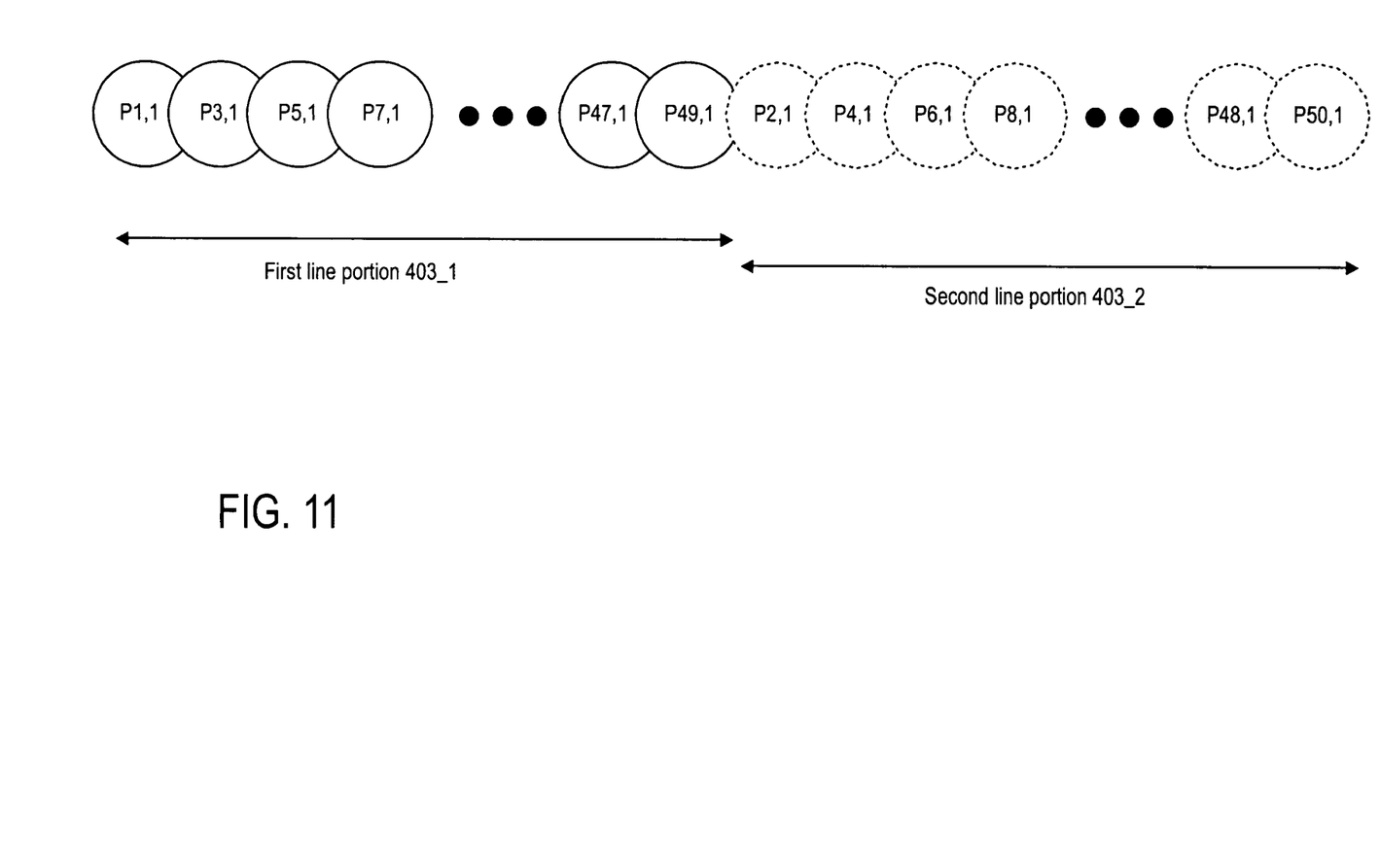
FIG. 11 illustrates a first line portion that is formed by multiple spots.

FIG. 11 illustrates a first line portion 403_1 that is formed by points P1,1; P3,1; P5,1; P7,1 . . . P47,1 and P49,1. A first line portion 403_1 is followed by second line portion 403_2 that is formed by points P2,1; P4,1; P6,1; P8,1 . . . P48,1 and P50,1. The first line portion 403_1 is imaged onto a single cell of a line CCD of sensor array 250 while the second line portion 403_2 is imaged onto a single cell of a line CCD of sensor array 251. Each cell of the CCD line array receives a continuous stream of light beams that form a continuous line.

The duty cycle of the line CCDs can reach almost 100%. State of the art line CCDs are characterized by an integration period T1 that is much longer than the discharge time from CCD cell to shift register cell T2. During an integration period the content of the shift register is sent to a storage unit.

According to another embodiment of the invention the spot array is rectangular shaped and includes one hundred rows and one hundred columns. Thus, the first imaginary line portion 403_1 will be formed by fifty spots of the first column P1,1-P1,50 and the second imaginary line portion 403_2 is formed by other fifty spots of the same first column P1,51-P1,100.

Figure 12:
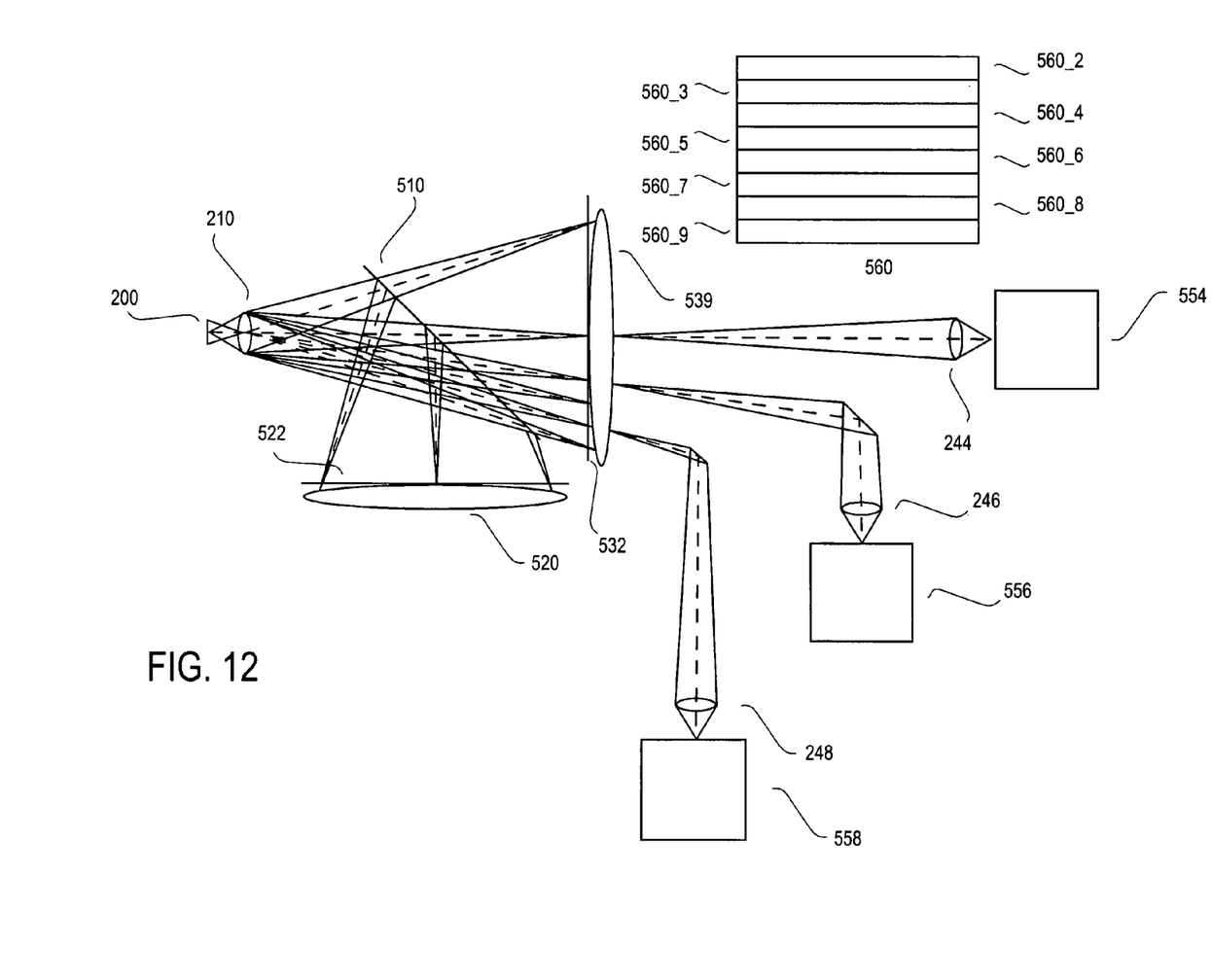
FIG. 12 illustrates various optical components, according to another embodiment of the invention.

FIG. 12 illustrates various optical components, according to another embodiment of the invention. The optical components include a beam splitter and large objective lenses instead of the Fresnel lens array.

A Scintillator 200 is followed by a magnifying lens 210 that in turn is followed by a beam splitter 510, optional field lenses 520 and 539, spatial filters 522 and 532, multiple imaging lenses 240-249 and multiple sensor arrays 550-559. The various optical components facilitate imaging of the whole light beam array, and compensate for the differences between the size of sensor array facets and the size of the light sensitive cells. Assuming that an intermediate image 560 is formed at the beam splitter 510 then the odd portions of that image 560_1, 560_3, . . . 560_9 are imaged by sensor arrays 551, 553, 555, 557 and 559 that are positioned to receive light that passes through field lens 520. The even portions 560_0, 560_2, . . . 560_8 are imaged by sensor arrays 550, 552, 554, 556 and 558 that are positioned to receive light that passes through field lens 539.

The sensor arrays may include CCD arrays, such as backside illuminated CCD arrays, but this is not necessarily so.

The beam splitter 510 directs an intermediate image of light beams towards each of the objective lenses 520 and 539. Spatial filters 522 and 532 may be positioned in proximity to the field lenses but they may also be replaced by a single spatial filter that is positioned along a path of the light beams, between the magnifying lens 210 and the beam splitter 510.

Figure 13:
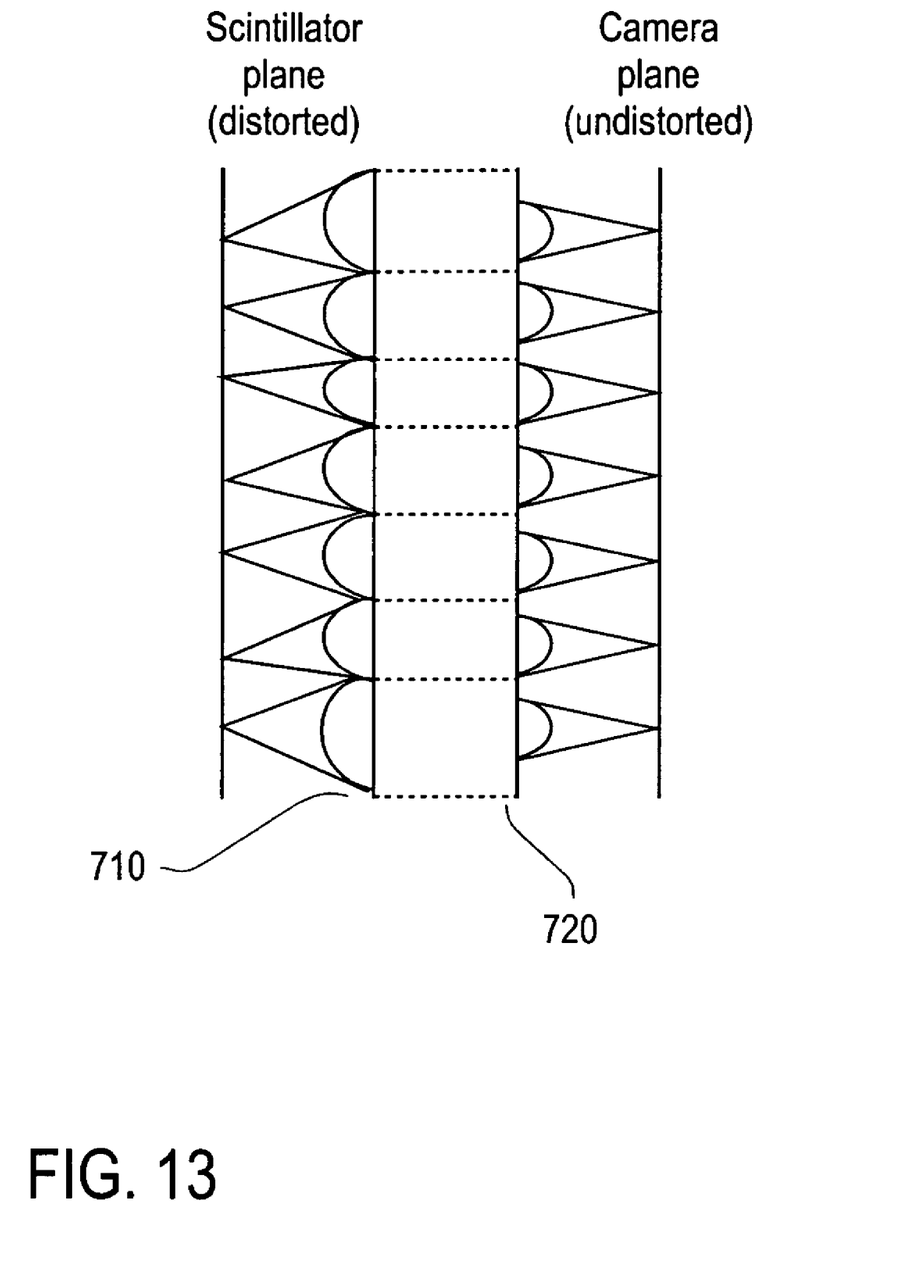
FIG. 13 illustrates another device for compensating for aberrations, according to an embodiment of the invention.

FIG. 13 illustrates another device for compensating for aberrations. The device 700 includes two arrays 710 and 720 of microlenses that face each other. The first microlens array 710 is shaped such that the location of focal points of the lenses corresponds to a distorted array, while the second array 720 is shaped such that the focal points of the lens form an ordered array.

The images can be processed by applying various comparison methods, such as die to die comparison, cell-to-cell comparison and die to database comparison.

While this invention has been described in connection with what is presently considered to be the most practical and preferred embodiment, it is to be understood that the invention is not limited to the disclosed embodiment. Rather, it is intended to cover various modifications within the spirit and scope of the appended claims.

What is claimed is:

1. A system, comprising:
multiple one dimensional detector arrays, each comprising a row of CCD light sensitive cells;
a two dimensional Fresnel lens array for directing multiple beams towards the multiple one dimensional detector arrays, the Fresnel lens array arranged as rows of lenses, each of said lenses arranged to direct a respective single one of said multiple beams towards a corresponding one of said CCD cells, wherein lenses of even rows of said Fresnel lens array direct respective beams towards CCD cells in even rows of said detector arrays and lenses of odd rows of said Fresnel lens array direct respective beams towards CCD cells in odd rows of said detector arrays in an interlaced manner.

2. A method for inspecting an article, the method comprising:
receiving multiple light beams; and
directing, by a two dimensional Fresnel lens array arranged as rows of lenses, said multiple light beams towards multiple one dimensional detector arrays, each comprising a row of CCD light sensitive cells, by arranging each of said lenses to direct a respective single one of said multiple beams towards a corresponding one of said CCD cells so that lenses of even rows of said Fresnel lens array direct respective beams towards CCD cells in even rows of said detector arrays and lenses of odd rows of said Fresnel lens array direct respective beams towards CCD cells in odd rows of said detector arrays in an interlaced manner.

* * * * *